United States Patent
Ranawat et al.

(10) Patent No.: US 9,125,669 B2
(45) Date of Patent: Sep. 8, 2015

(54) HAPTIC VOLUMES FOR REAMING DURING ARTHROPLASTY

(75) Inventors: Amar Ranawat, New York, NY (US);
Mark Pagnano, Chatfield, MN (US);
Lawrence Dorr, La Canada, CA (US);
Richard Jones, Dallas, TX (US);
Danielle Landeck, Delray Beach, FL (US); Matt Thompson, Durham, NC (US); Radu Iorgulescu, Boca Raton, FL (US); Renen Bassik, Miami, FL (US);
Daniel Odermatt, Fort Lauderdale, FL (US)

(73) Assignee: MAKO Surgical Corporation, Fort Lauderdale, FL (US)

( * ) Notice: Subject to any disclaimer, the term of this patent is extended or adjusted under 35 U.S.C. 154(b) by 530 days.

(21) Appl. No.: 13/173,868

(22) Filed: Jun. 30, 2011

(65) Prior Publication Data

US 2012/0209272 A1  Aug. 16, 2012

Related U.S. Application Data

(60) Provisional application No. 61/442,534, filed on Feb. 14, 2011.

(51) Int. Cl.
| | |
|---|---|
| A61F 2/46 | (2006.01) |
| A61B 17/00 | (2006.01) |
| A61B 17/16 | (2006.01) |
| A61B 19/00 | (2006.01) |

(52) U.S. Cl.
CPC .......... *A61B 17/1666* (2013.01); *A61B 17/1626* (2013.01); *A61B 19/2203* (2013.01); *A61B 2019/2292* (2013.01)

(58) Field of Classification Search
CPC ......... A61B 17/8847; A61B 17/1664–17/1666
USPC .............. 606/79–81, 86 R; 623/22.11–22.29
See application file for complete search history.

(56) References Cited

U.S. PATENT DOCUMENTS

| | | | |
|---|---|---|---|
| 2004/0034302 A1* | 2/2004 | Abovitz et al. ............... 600/428 |
| 2004/0092944 A1* | 5/2004 | Penenberg ....................... 606/91 |
| 2005/0273109 A1* | 12/2005 | Bjork .............................. 606/80 |
| 2006/0129157 A1* | 6/2006 | Desarzens et al. .............. 606/81 |

* cited by examiner

*Primary Examiner* — Matthew Lawson
(74) *Attorney, Agent, or Firm* — Miller, Matthias & Hull LLP

(57) ABSTRACT

A haptic robotic system for reaming an acetabulum prior to inserting an acetabular cup is more accurate than conventional instruments and may reduce the risk of dislocation and improve durability of a hip implant. Disclosed is a three-dimensional tool path, referred to as a haptic volume. Once the haptic volume is implemented into the software of a haptically constrained surgical robotic system, the cutting tool or reamer can only be utilized within the haptic volume. The haptic volume guides the surgeon in preparing the final reamed bone surface with a greatly reduced chance of the reaming unintended bone and greatly increases the chance that the reaming procedure may be carried out using one reaming tool, or using a single-stage reaming process.

17 Claims, 7 Drawing Sheets

HAPTIC VOLUMES FOR REAMING DURING ARTHROPLASTY

TECHNICAL FIELD

This disclosure relates generally to robotic systems and, more specifically, to haptically controlled surgical robotic systems for surgically sculpting bone. In the case of orthopedic joint replacement surgeries, for example, this disclosure relates to haptic volumes used for reaming bone where desired and which can prevent the unwanted reaming of healthy bone. Still more specifically, this disclosure relates to haptically controlled robotic systems and haptic volumes for reaming an acetabulum prior to installation of an acetabular cup during total hip arthroplasty (THA).

BACKGROUND AND DESCRIPTION OF THE RELATED ART

Robotic systems are often used in applications that require a high degree of accuracy and/or precision, such as surgical procedures or other complex tasks. Such systems may include various types of robots, such as autonomous, teleoperated, and interactive. This disclosure is directed towards interactive robotic systems with haptic control.

Interactive robotic systems are preferred for some types of surgery, such as joint replacement surgery, because they enable a surgeon to maintain direct, hands-on control of the surgical procedure while still achieving a high degree of accuracy and/or precision. For example, referring to FIGS. 1-3, in hip replacement surgery, a surgeon can use an interactive, haptically guided robotic arm equipped with a semi-spherical cutting tool or cutting tool 23 in a passive manner to sculpt a semi-spherical indentation in the acetabulum 21, which is a cup-shaped socket in the pelvis 22. The acetabulum 21 receives a cup commonly referred to as an acetabular cup (not shown) that, in turn receives a resurfaced femoral head in a partial hip arthroplasty or, in the case of a total hip arthroplasty (THA), the ball portion of the hip implant. To sculpt bone or, in this example, the portion of the acetabulum 21 where the cup is to be located, the surgeon manually grasps and manipulates the robotic arm 20 to move a cutting tool or cutting tool 23 that is coupled to the robotic arm. As long as the surgeon maintains the cutting tool within a predefined virtual cutting boundary defined by a straight line haptic path, the surgeon can move the robotic arm freely with low friction and low inertia. However, if the surgeon attempts to move the cutting tool to cut bone off of the haptic path, the robotic arm provides haptic (or force) feedback that prevents or inhibits the surgeon from moving the cutting tool beyond the virtual cutting boundary.

In other types of surgeries, haptic volumes are used instead of straight-line haptic paths. For example, as disclosed in commonly assigned US2006/0142657, haptic volumes having various geometric volumes may be modeled using planes, spheres, cones, cylinders, etc.

Returning to hip replacement surgeries, such as THAs, surgical robotic tools are typically limited haptically to a straight line path, normal to where the rim of the planned cup will be after installation or possibly offset a known distance from the planned central axis of the acetabular cup. The semi-spherical cutting tool 23 that is extended along a straight line results in a reamed volume that is cylindrical in shape, except at the semi-spherical end. The intention of a straight line haptic path is to constrain the center of the semi-spherical cutting tool 23 along a path that is normal to the rim of the planned acetabular cup and to provide a semi-spherical reamed end for receiving the cup. To avoid unintended reaming and inaccurate bone preparation, if the center of the cutting tool 23 is not maintained along the straight line haptic path, the controller may not allow the cutting tool 23 to operate.

The above-described interactive robotic system, though useful for THA, is not optimally suited for THA and other types of replacement surgeries that require the use of multiple surgical tools having different functions (e.g., reaming, impacting), different configurations (e.g., straight, offset), different sizes (e.g. multiple cutting tools of different sizes) and different weights. A system designed to accommodate a variety of tools may be prohibitively complex for haptic control because it would require removing and attaching different types of tools to the robotic arm during a surgical procedure which may affect the accuracy of the haptic path and could increase the time needed to perform the procedure.

Further, in THA, in addition to maintaining an appropriate cutting boundary, an angular orientation of surgical tools and implants is important. For example, in conventional THA, the surgeon uses the semi-spherical cutting tool 23 (FIG. 2) to resurface the acetabulum 21 (FIG. 1). Then, an acetabular cup is attached to a distal end of an impactor tool (not shown). The surgeon implants the acetabular cup into the reamed socket by repeatedly striking a proximal end of the impactor tool with a mallet. Angular orientation of both the reamed socket and the implanted acetabular cup is important because incorrect orientation can result in misalignment of the acetabular cup away from the appropriate version and inclination angles of the acetabular anatomy. Misalignment can lead to post-operative problems, including joint dislocation, impingement of the femur on the acetabular cup at extreme ranges of motion, and accelerated wear of the acetabular cup due to improper loading of the femoral head-to-acetabular cup interface. Alignment is also important to maintain correct leg length and medial/lateral offset. Even more problematic, recent advances in THA reveal that the ideal acetabular cup position is in a narrower range than previously appreciated and that acetabular cup position is dependent on femoral component anteversion.

Use of a straight line haptic path or straight line reaming does not allow for a single-stage reaming process in most cases. Specifically, the surgeon typically uses cutting tools of different sizes in order to achieve the correct size and orientation for the acetabular cup. Single stage reaming is desirable because it is fast, reduces the possibility of infection and reduces operating room time. However, a straight line haptic path is not possible, for example, if the tool center is pushed away from the haptic path by the surface of the acetabular rim. Because the center of the cutting tool is pushed off the haptic path in these cases, before the bowl-shaped indentation for the cup is reamed, the surgeon is required to employ multi-stage reaming with different cutting tools or ream free-handed without the benefits of haptic constraint.

For at least these reasons, more accurate acetabular cup positioning techniques will be important because it is well known that misalignment of the acetabular component in THA may result in dislocation, reduced range of motion or accelerated wear. Further, improved haptic control systems for hip replacement and other surgeries are needed that afford the surgeon some additional flexibility while still employing haptic control.

SUMMARY OF THE DISCLOSURE

In a refinement, a haptic robotic surgical system for reaming an indentation in a bone of a patient is disclosed. The system includes a cutting tool and a controller that is programmed to compare an intended indentation in the bone and a position of the cutting tool when placed proximate to the bone. The controller is also programmed to generate a haptic volume that includes a tapered section that narrows as the haptic volume extends towards the bone. The controller is also programmed to generate control signals that will allow movement of the cutting tool within the haptic volume and provide haptic feedback to constrain movement of the cutting tool outside of the haptic volume.

Improved parabolic haptic volumes for both single-stage reaming and multi-stage reaming are also disclosed by way of Equations (1) and (2) below.

In another refinement, a method for reaming an indentation in an acetabulum of a patient. The method includes determining a location for a intended indentation in the acetabulum including a bottom point where a central axis of a final indentation intersects the intended indentation, selecting a cutting tool having a radius, placing the cutting tool at an initial position on the acetabulum, comparing the intended indentation on the acetabulum and the initial position of the cutting tool on the acetabulum, and generating a haptic volume that includes a tapered section that narrows as the haptic volume extends towards the acetabulum. The method also includes allowing movement of the cutting tool within the haptic volume and providing haptic feedback to constrain movement of the cutting tool to within the haptic volume.

In another refinement, a haptic robotic surgical system for total hip arthroplasty (THA) surgeries is disclosed. The system includes a cutting tool and a controller. The controller is programmed to compare an intended indentation in the acetabulum and a position of the cutting tool when initially placed on the acetabulum. The controller is also programmed to generate a haptic volume that includes a tapered section that narrows as the haptic volume extends towards the acetabulum and a straight line section disposed between the tapered section and the acetabulum. The controller is also programmed to generate control signals that will allow movement of the cutting tool within the haptic volume and provide haptic feedback to constrain movement of at least a portion of the cutting tool to within the haptic volume.

A method for reaming an indentation in an acetabulum of a patient is disclosed. The method includes determining a location for an intended indentation in the acetabulum including a bottom point where a central axis of a final indentation intersects the intended indentation; selecting a cutting tool having a radius larger or smaller than the final indentation; placing the cutting tool at an initial position proximate to the acetabulum; comparing the intended indentation on the acetabulum and the initial position of the cutting tool on the acetabulum; generating a haptic volume including a tapered section that narrows as the haptic volume extends towards the acetabulum; allowing movement of the cutting tool within the haptic volume and providing haptic feedback to constrain movement of the cutting tool to within the haptic volume; wherein, if the final indentation has a diameter that is about equal to a diameter of the selected tool, generating the haptic volume from Equation (1):

$$r(h) \leq R - \sqrt{R^2 - h^2} \text{ when } h \text{ is } < R \quad (1)$$

where R is the radius of the intended indentation and h is a distance between an outer surface of the acetabulum and r on the outer surface of the parabolic tapered section; and wherein, if the final indentation has a diameter that greater than a diameter of the selected tool, generating the haptic volume from Equation (2):

$$r(h) \leq R - \sqrt{R^2 - h^2} + (2R - d)/2, \text{ when } d < 2R \text{ and } h < R \quad (2)$$

where d is the selected tool diameter.

Other advantages and features will be apparent from the following detailed description when read in conjunction with the attached drawings.

DETAILED DESCRIPTION OF THE PRESENTLY PREFERRED EMBODIMENTS

Figure 4:
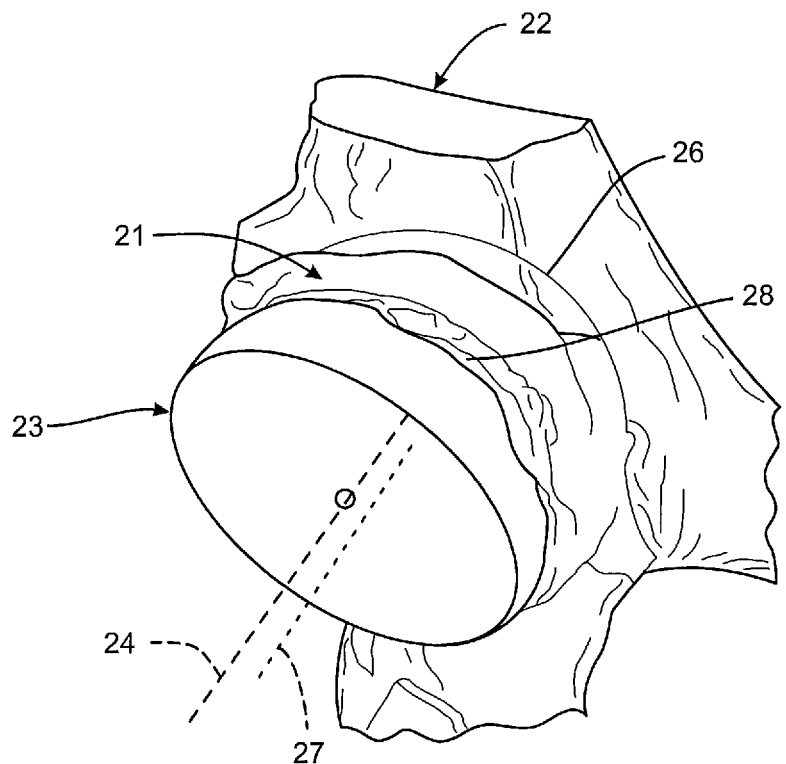
FIG. 4 illustrates the deficiencies of using a straight line haptic path in the event the architecture of the acetabulum or the acetabular rim engages the cutting tool when the cutting tool is initially placed against the acetabulum thereby causing the center of the cutting tool to be offset from the straight-line haptic path which may cause the system to render the cutting tool inoperable.

Turning to FIG. 4, in order to accommodate single-stage reaming, the cutting tool 23 may be within the haptic constraint of the system (not shown in FIG. 4) even when the central axis 24 of the cutting tool 23 is not co-linear with the intended cup normal or central axis 25 of the intended indentation 26, yet not compromise the final location and shape of the indentation 26. Specifically, in FIG. 4, the cutting tool 23 has been placed against the acetabulum 21 but the surgeon is unable to position the cutting tool 23 so that its central axis 24 is co-linear with the intended tool path or the straight-line haptic path 27 because of interference between the cutting tool 23 and the acetabular rim 28. In other words, the architecture of the acetabulum 21 prevents the surgeon from placing the cutting tool 23 in an initial position that would allow a single-stage reaming process defined by the haptic path 27. Thus, prior to this disclosure, a multiple-stage reaming process would need to be carried out which requires the surgeon to use multiple cutting tools 23 of different sizes. Multi-stage reaming increases the amount of time needed for the surgery, the amount of operating room time consumed and, because multiple cutting tools 23 of different sizes would be used, may also increase the possibility of infection.

Figure 5:
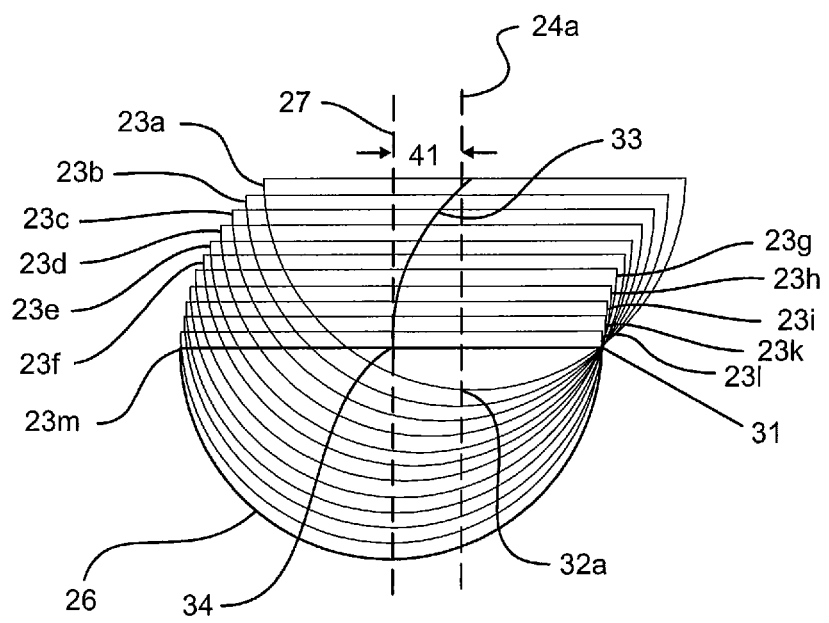
FIG. 5 illustrates, schematically, a widest possible path that a semi-spherical cutting tool can take without disrupting the shape of the intended indentation.
Figure 6:
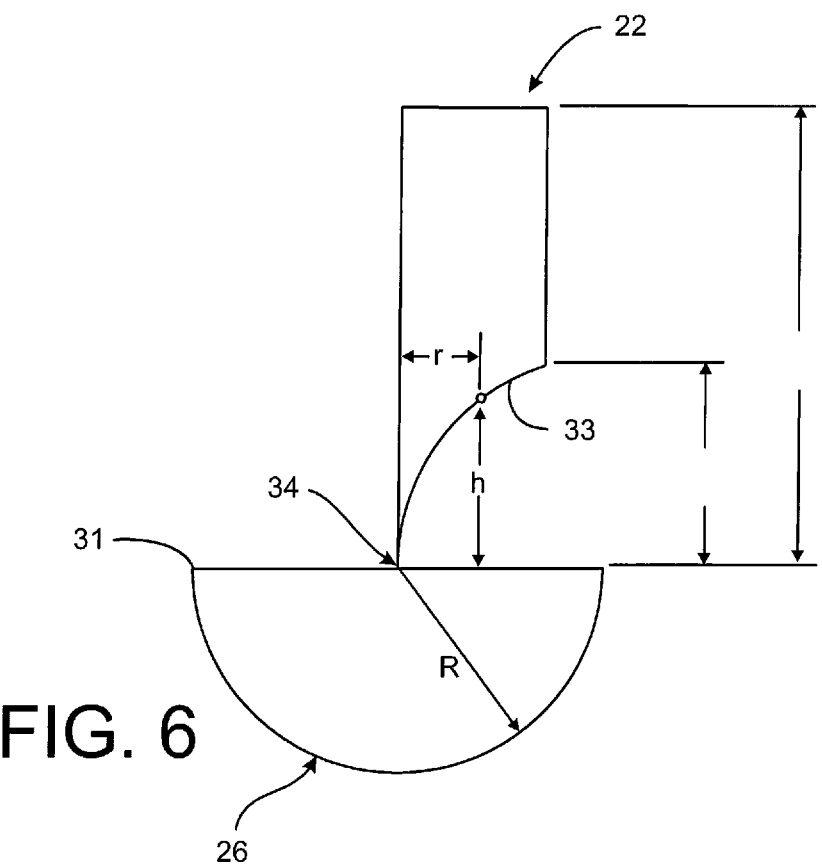
FIG. 6 illustrates, schematically and in two dimensions, a parabolic haptic path for development of a parabolic haptic volume.
Figure 7:
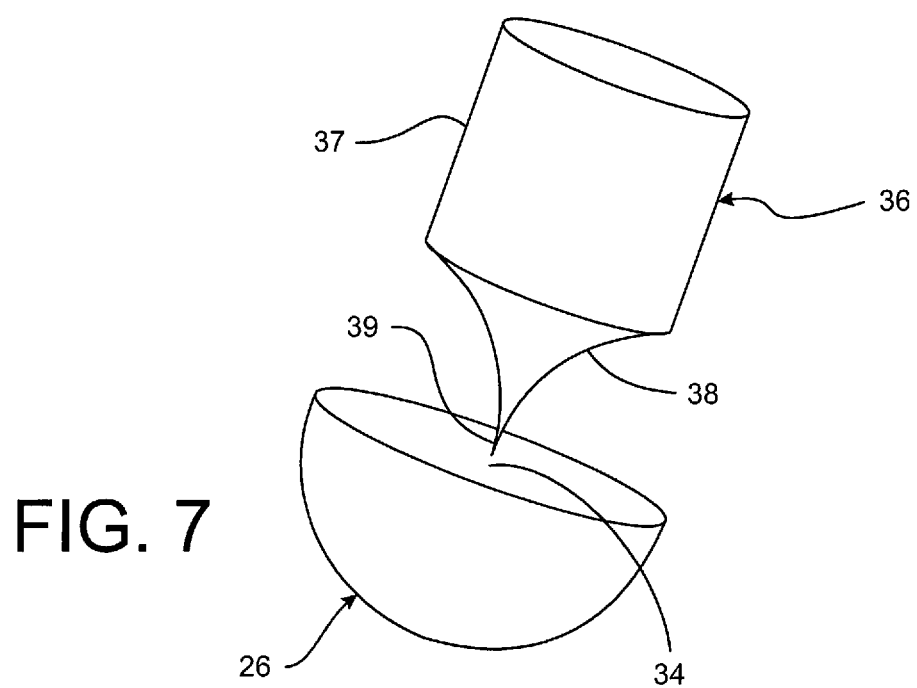
FIG. 7 illustrates, schematically and in three dimensions, a parabolic haptic volume disposed above a semi-spherical indentation or final reamed surface.
Figure 10:
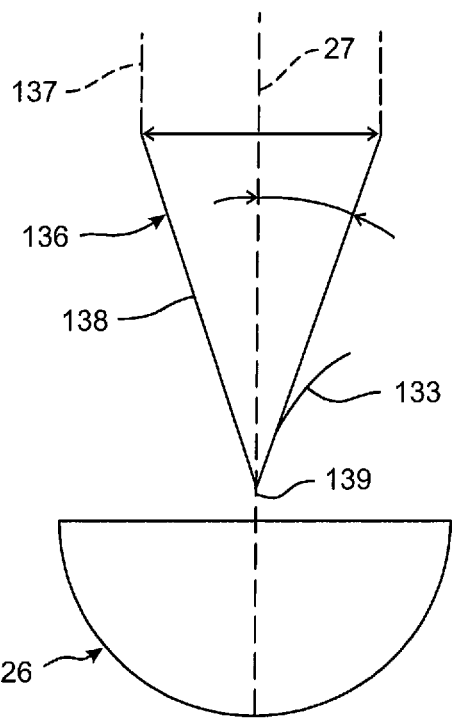
FIG. 10 illustrates, schematically and in two dimensions, a haptic volume that includes a conically-shaped section, a cylindrical section disposed above and a straight-line section disposed below the conically-shaped section as well as an intended semi-spherical indentation.
Figure 11:
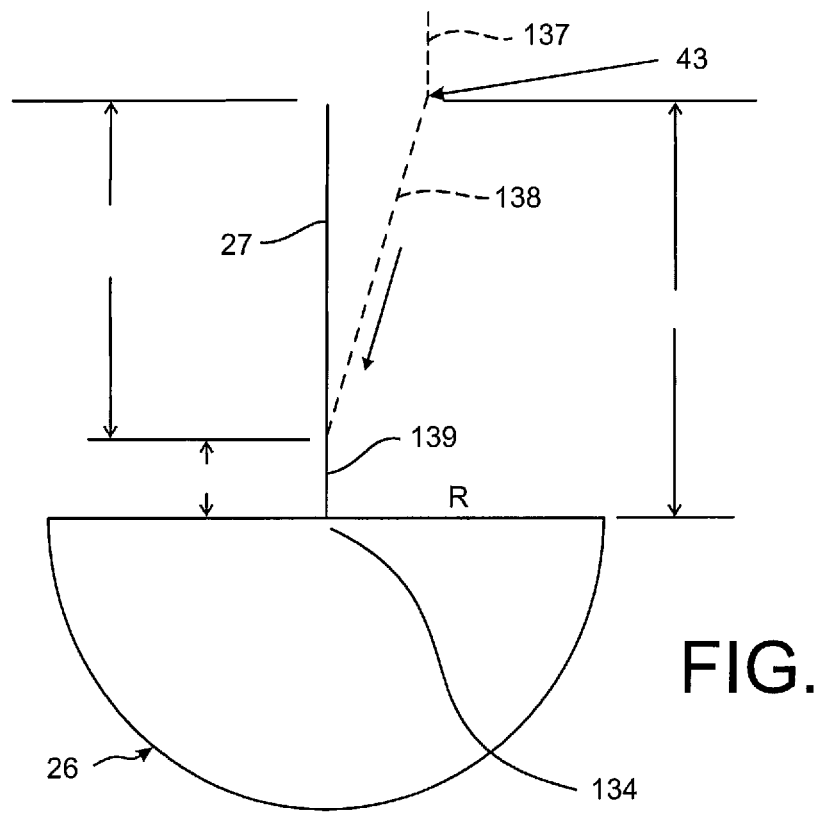
FIG. 11 illustrates, schematically and in two dimensions, the initial deviated path that a cutting tool may take prior to passing into the straight-line section of the haptic volume illustrated in FIG. 10.
Figure 12:
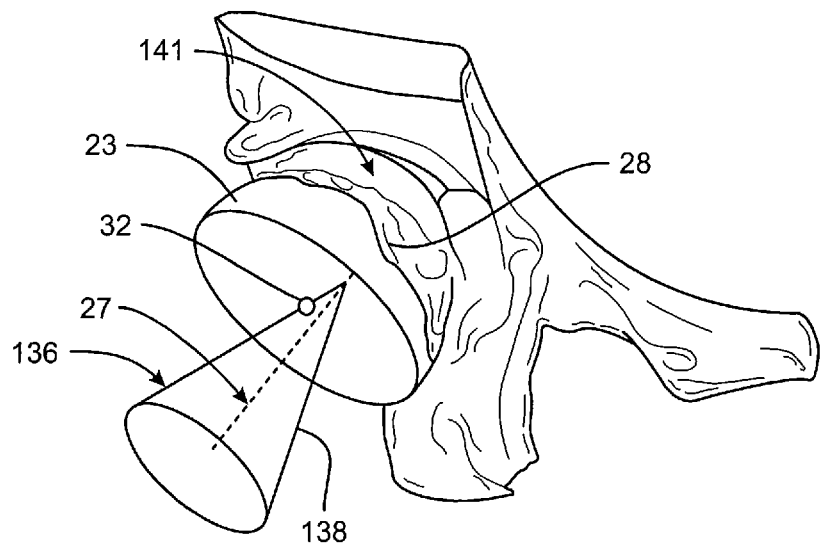
FIG. 12 is a perspective view of an acetabulum, acetabular rim, cutting tool, conically-shaped haptic volume, original straight-line haptic path and planned position of the indentation in the acetabulum.

One solution to the problem illustrated in FIG. 4 is provided by one aspect of this disclosure illustrated in FIGS. 5-7 and another aspect of this disclosure illustrated in FIGS. 10-12.

Part of the solution to the problem illustrated in FIG. 4 is shown in FIG. 5. Specifically, the final reamed surface or intended indentation 26 is illustrated with a central axis 27. The initial position of the cutting tool 23 on the acetabulum 21 and the acetabular rim 28 (see FIG. 4) is shown at 23a. Clearly, the central axis 24a of the cutting tool 23, while in the position shown at 23a, is offset from the central axis 27 of the intended indentation 26. If a surgeon were to follow the central axis 24a, the location of the final indentation (not shown) would be offset from the location of the intended indentation 26. However, because the position of the cutting tool shown at 23a does not interfere with the intended rim 31 of the indentation 26, reaming may begin from the position shown at 23a. However, a straight path cannot be taken and, instead, a curved or parabolic path 33 may be used instead. The parabolic path 33 represents the maximum displacement of the central axis shown at 24a or the tool center shown at 32a (see also the bottom center 32 in FIG. 2) and the central axis 27 of the intended indentation 26. By following the parabolic path 33, one can see the position of the cutting tool 23 moving from the position shown at 23a to the position shown at 23b, 23c, 23d, etc. until the cutting tool 23 reaches its final position shown at 23m which coincides with the intended indentation 26. Thus, a curved or parabolic path 33 provides for more opportunities for a single stage reaming process and, as shown in FIGS. 6-7 below, provides greater flexibility for the surgeon.

Figure 1:
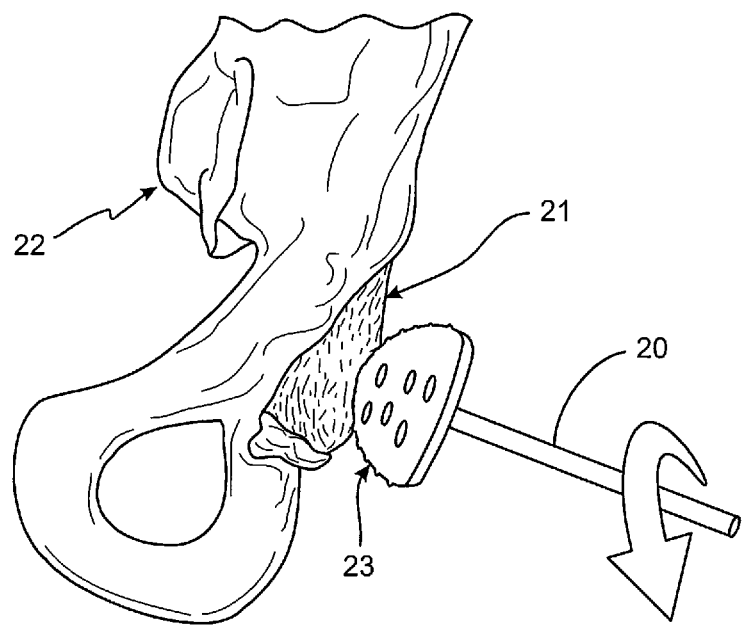
FIG. 1 is a perspective view of a cutting tool mounted on an arm and engaging an acetabulum of a pelvis.
Figure 2:
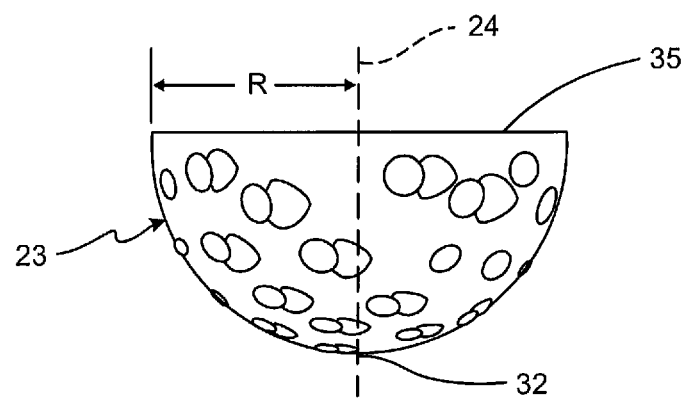
FIG. 2 is a plan view of a semi-spherical cutting tool.
Figure 3:
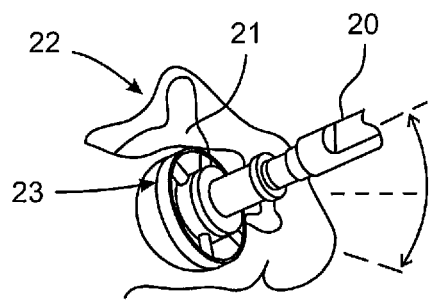
FIG. 3 is another perspective view of a cutting tool mounted on an arm and engaging an acetabulum of a pelvis during the reaming of a semi-spherical indentation in the acetabulum.

Turning to FIG. 6, the parabolic path 33 allows for the greatest radial translation of the bottom center 32 (see FIG. 2) of the cutting tool 23 without over-reaming the intended indentation 26, particularly at its rim 31. The specific shape of the tool path 33 is dependent on the diameter or radius of the final indentation 26 but is asymptotic as the path 33 approaches the tool end point 34 or the maximum depth reached by the upper rim 35 of the cutting tool 23 as shown in FIG. 2. In order to avoid disrupting the shape of the intended indentation 26, or in order to avoid over-reaming, the radial translation r of the bottom center 32, at a height h above the tool end point 34, must be less than or equal to final indentation radius R (see also FIG. 2) minus the square root of $(R^2-h^2)$ as shown by Equation 1:

$$r(h) \leq R - \sqrt{R^2-h^2} \text{ when } h \text{ is} < R \quad (1)$$

The three dimensional volume of the parabolic path 33 is shown in FIG. 7. A haptic volume 36 may include an initial cylindrical section 37 that leads to a parabolic section 38 that is defined by Equation 1 and that may optionally lead to a short straight-line section 39 where the tangents of the narrow portion of the parabolic curve are vertical lines. The bottom of the parabolic section 38 as shown at 39 intersects with the tool end point 34. Despite the offset 41 between the central axis 24a of the cutting tool 23 when it initially engages the acetabular rim 28 and acetabulum 21, the intended indentation 26 may still be reamed using a single cutting tool 23 or a single-stage process.

For procedures where single stage reaming is not desired or practical, Equation 1 may be modified so that to allow smaller reamers of a diameter d to ream a larger cavity having an intended radius R where 2R>d for conducting multi-stage reaming (i.e., not single-stage reaming). The revised equation is presented below as Equation 2:

$$r(h) \leq R - \sqrt{R^2-h^2} + (2R-d)/2, \text{ when } d<2R \text{ and } h<R \quad (2)$$

Figure 8:
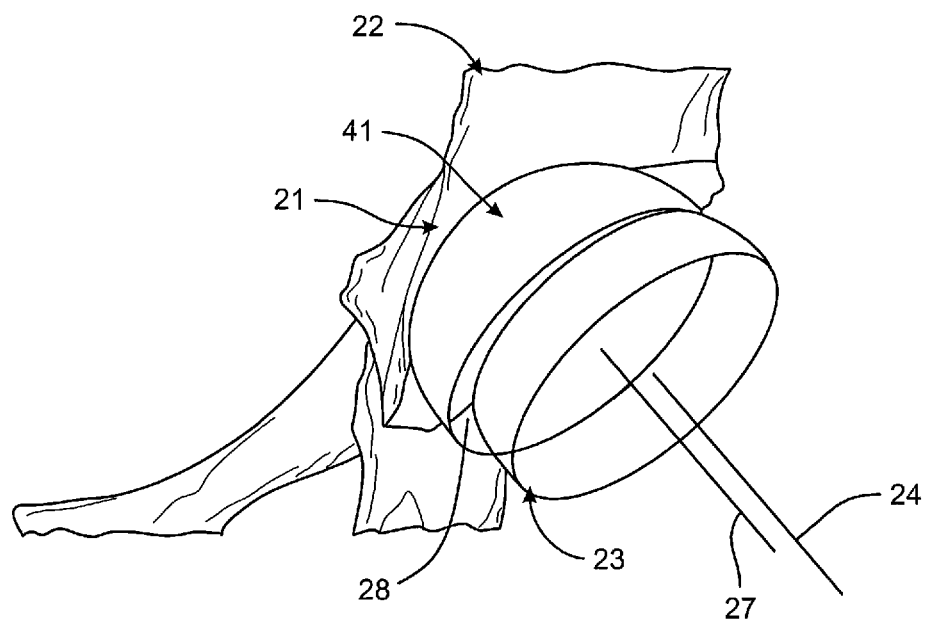
FIG. 8 illustrates the placement of a semi-spherical cutting tool on an acetabular rim of an acetabulum which causes the central axis of the cutting tool to be offset from the central axis of the planned indentation.
Figure 9:
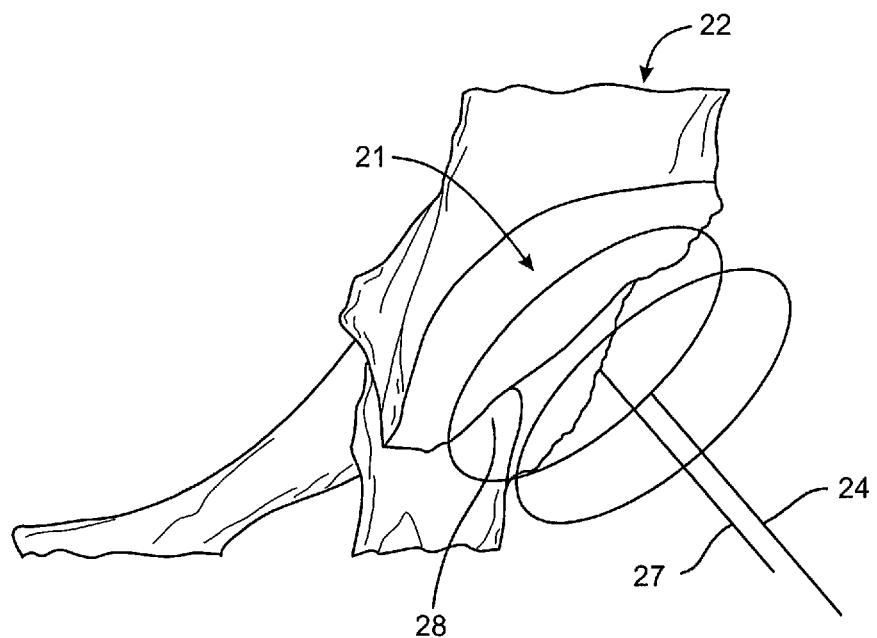
FIG. 9 illustrates a measurement of a distance between the central axis of the cutting tool as shown in FIG. 8 from the central axis of the planned indentation as shown in FIG. 8.

FIG. 8 illustrates the placement of the cutting tool 23 on the acetabular rim 28 which causes the initial misalignment between the cutting tool 23 and the intended placement of the acetabular cup 41. FIG. 9 illustrates the measurement of the offset between the central axis 24 of the cutting tool 23 and the central axis 27 of the planned cup placement or the intended indentation 26.

Figure 13:
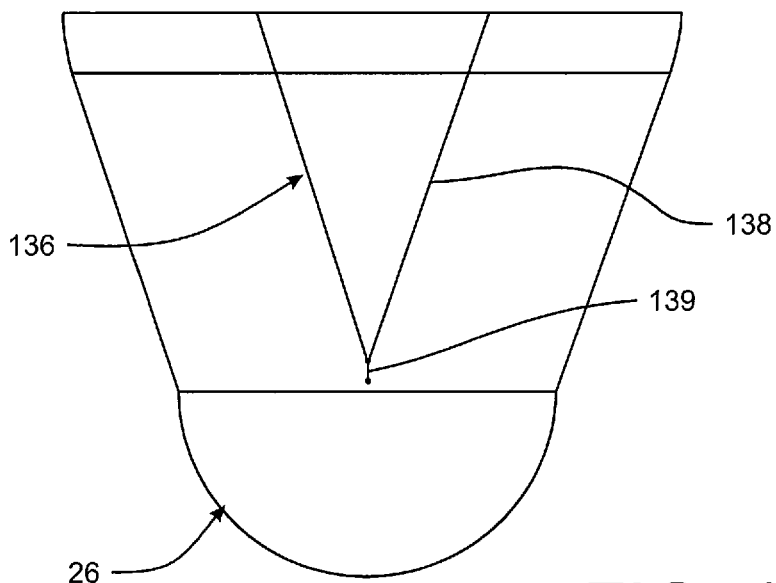
FIG. 13 illustrates a maximum volume of a tool path taken by a semi-spherical cutting tool that follows the boundaries of the conically-shaped haptic volume illustrated in FIGS. 10-12.

In a refinement, FIGS. 10-13 illustrate the use of conically-shaped haptic volumes 136 which may include an initial cylindrical section 137 which leads into the conical section 138, which is tapered as it extends to the straight line section 139. Because of the conical section 138 of the haptic volume 136, the largest possible volume created using this technique or tool path is also conical in shape as shown in FIG. 13, which is in contrast to the cylindrical tool volumes of prior art straight-line haptic reaming paths. In the embodiment illustrated in FIG. 10, the vertex angle of the conical section 138 is 38° and the half vertex angle between the central axis 27 and the outer boundary of the conical section 138 is 19°. The half vertex angle can vary greatly and can range from about 10° to about 30°, more preferably from about 12° to about 23°, still more preferably from about 15° to about 20° and still more preferably from about 16° to about 19°. While the half vertex angle 19° may be increased to increase the possibility of reaming the intended indentation 26 in a single-stage process, the same goal may be achieved by switching to a parabolic-shaped haptic volume as indicated by the parabolic line 133 as shown in FIG. 10.

FIG. 11 illustrates, schematically, a cutting tool 23 that is initially offset from an intended end point 134 and the central axis 27 of the indentation 26. An initial straight-line reaming may be carried out in the cylindrical section shown at 137, but haptic control may be initiated at the base 43 of the conical section 138. The boundary of the conical section 138 and the boundaries of the other haptic volumes discussed herein, represent the widest path that the bottom center 32 of the cutting tool 23 can take before it reaches the straight line section 139 which insures that the axes 24, 27 of the cutting tool 23 and indentation 26 respectively are co-linear as the cutting tool 23 reaches the tool end point 134.

FIG. 12 illustrates the employment of this method. The planned cup position is shown at 141 and interference by the acetabular rim 28 causes the initial placement of the cutting tool 23 to be offset from the central axis 27 of the planned indentation 26, which causes the bottom center 32 of the cutting tool 23 to be offset from the central axis 27, which may also be referred to as the original haptic path, the conventional haptic path or the straight line haptic path. However, the bottom center 32 of the cutting tool 23 is disposed along the boundary of the conical section 138 of the haptic volume 136.

Figure 14:
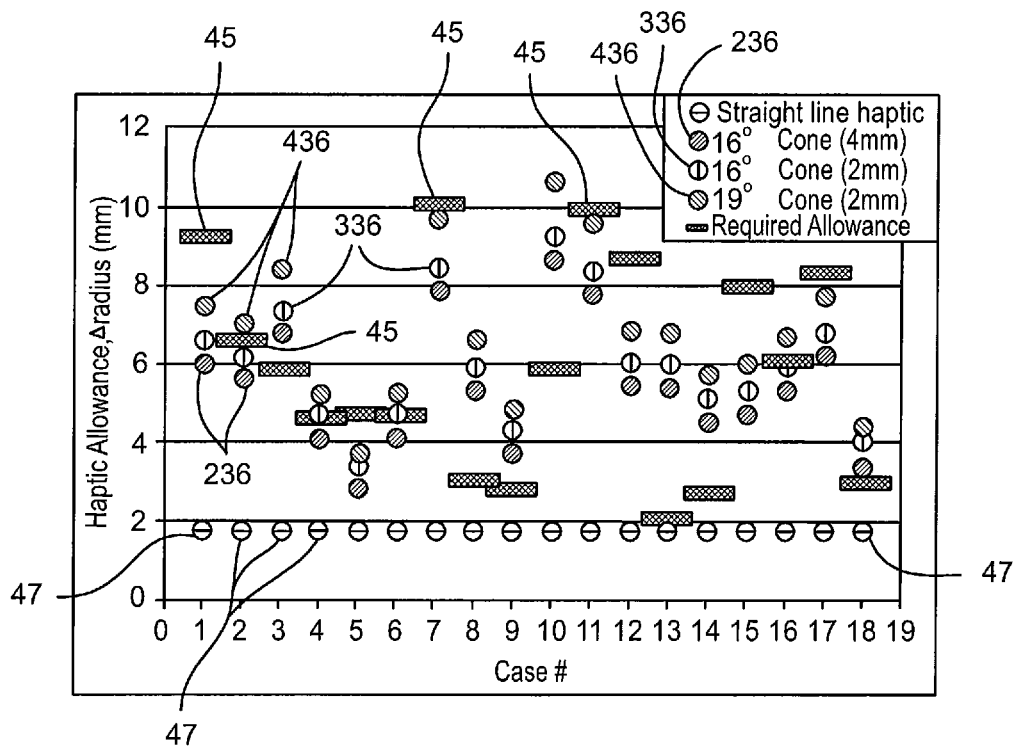
FIG. 14 illustrates, graphically, the haptic allowance or the distance between the central axis of the semi-spherical cutting tool and a straight-line haptic path for 18 different patients and the haptic allowance provided by three different conically-shaped haptic volumes.
Figure 15:
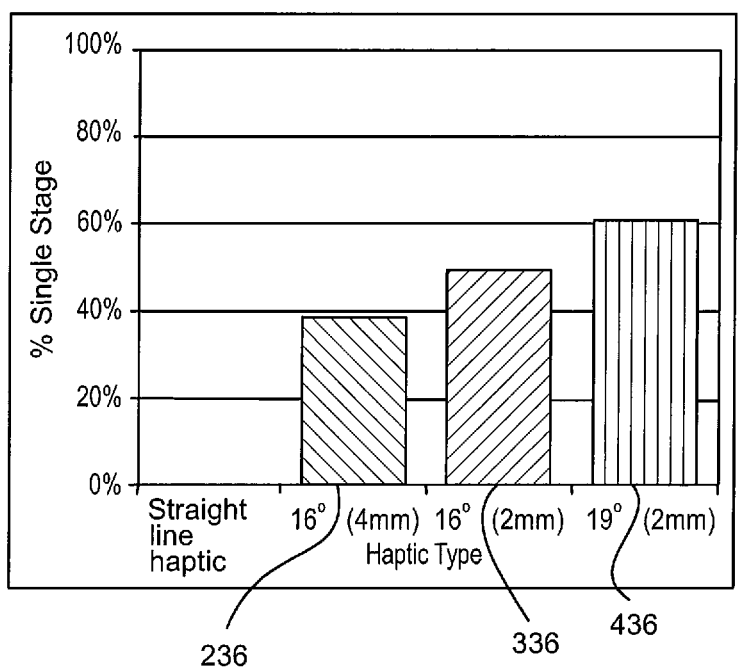
FIG. 15 is a bar graph illustrating the percentage of the 18 cases of FIG. 14 that the three different haptic volumes can accommodate in a single-stage reaming process, particularly illustrating that the greatest degree of success is provided by the conically-shaped haptic volume with a 19° half vertex angle and that none of the 18 cases can be reamed using a single-stage process and a straight-line haptic path.

Simulated data for three different conically-shaped haptic volumes are graphically illustrated in FIGS. 14-15. Specifically, the horizontal marks shown at 45 illustrate the required allowance or the distance between the bottom center 32 of the cutting tool 23 when it is initially placed on the acetabulum 21 and a straight-line haptic path with a 2 mm variance as indicated by the small circles with the horizontal lines and shown at 47. FIGS. 14-15 represent simulated data based on 18 different histories. As can be seen from FIG. 14, the distance between the horizontal marks 45 and the straight line haptic marks 47 vary from case to case. If this distance is too great, such as for case number 1 in FIG. 14, each of the haptic volumes 236, 336 and 436 fail to provide a sufficient amount of haptic allowance in order for the cutting tool 23 to reach its final destination and form the intended indentation 26 at the correct place in a single-stage reaming process. However, for case number 2, the haptic volume 436 with the half vertex angle of 19° and a 2 millimeter straight line section (see 139 in FIG. 10) provides for a sufficient haptic allowance as indicated by the circle representing the haptic volume 436 being disposed above the horizontal mark 45, thereby indicating that the haptic volume 436 with a 19° half vertex angle and a 2 millimeter straight line section 139 (FIG. 10) can be used for case number 2 and a single-stage reaming process may be carried out. In other words, for purposes of understanding FIG. 14, a haptic volume provides sufficient haptic allowance in order to enable a single-stage reaming process when a mark indicative of a haptic volume 236, 336, 436 is disposed above its corresponding horizontal mark 45. This means that the haptic volume 236, 336, 436 provides enough haptic allowance to compensate for the presence of the acetabular rim or other structure that otherwise would prevent the use of a single-stage reaming process. Thus, FIG. 14 shows that for some, but not all cases, a single-stage reaming process is available.

Specifically, the haptic volume 436 with the 19° half vertex angle and the two millimeter straight-line section 139 enables 11 of the 18 cases to be reamed with a single-stage reaming process (61%). In contrast, the haptic volume 336 with the 16° half vertex angle and the two millimeter straight-line section 139 enables 9 of the 18 cases to be reamed in a single-stage reaming process (50%) while the haptic volume 236 with the 16° half vertex angle and 4 millimeter final straight-line section 139 provides the least amount of haptic allowance and enables 7 of the 18 cases to be reamed in a single-stage reaming process (39%). It will be noted that straight-line sections such as straight line section 39 of FIG. 7 are not necessary for parabolic haptic volumes like the haptic volume 36. In contrast, for conical haptic volumes like the haptic volume 136 of FIG. 10, the straight line section 139 is needed. A straight-line section that is too long can be detrimental to the possibility of a single-stage reaming when using conical haptic volumes as shown by comparing the results for the haptic volumes 236 and 336. For example, the straight line section 39 of FIG. 7 or the straight line section 139 of FIG. 10 may have a length ranging from about 0 to about 6 mm, such as, a length ranging from about 2 to about 4 mm.

INDUSTRIAL APPLICABILITY

The haptic volume is designed to preserve the integrity of the bone surface required for primary stability of the implant, while providing flexibility to ream the acetabulum. This is achieved by defining the shape and dimensions of the haptic volume that accommodate the surgical technique used for reaming during traditional THA surgery with minimal constraints on the surgeon. The haptic or tactile feedback does not constrain the orientation of the reamer shaft but only the position of its center of rotation. This allows the surgeon to pivot the reamer shaft during reaming to maximize the cutting surface while preserving the bone that will support the implant. In addition, the tactile boundaries were designed to be curvilinear to ensure fluid transitions between the different sections of the haptic volume and replicate the standard reaming technique. Finally, the system will automatically detect the position of the reamer center relative to the haptic volume and will provide a signal to the user indicating that the cutting tool is within the tactile boundaries.

As noted above in connection with FIGS. 14-15, a straight-line haptic is not possible in many cases as the cutting tool center is pushed away from the intended path by the surface of the acetabular rim. In such a case, since the cutting tool or reamer center cannot be translated to its intended path, the surgeon would be required to multi-stage ream or ream freely with no haptic constraint. Typically, surgeons must employ a multi-stage reaming procedure where they use several reamer sizes before using the final planned reamer to prepare the final indentation or surface.

While a single-stage reaming procedure is preferred because of reduced operating room times, shorter operations and possibly a reduction in likelihood of infection during the reaming procedure as the reaming procedure is done faster and with fewer instruments than a multi-stage reaming procedure, reaming with smaller tools is sometimes preferable and a preferred multi-stage haptic volume is provided by Equation 2. The remaining disclosed parabolic and conical haptic volumes, surgical systems and methods increase the likelihood that a single-stage reaming process can be carried out with the attendant advantages.

The invention claimed is:

1. A haptic robotic surgical system for reaming an indentation in a bone of a patient, the system comprising:
    a cutting tool including a central axis aligned with a bottom center of the cutting tool; and
    a controller programmed to:
    compare an intended indentation in the bone and a position of the cutting tool when placed proximate to the bone, the central axis of the cutting tool being offset from a central axis of the intended indentation;
    generate a haptic volume through the bone comprising a tapered section that narrows as the haptic volume extends inward through the bone based at least in part on the comparison of the intended indentation in the bone and the position of the cutting tool when placed proximate to the bone; and
    generate control signals that will allow movement of the cutting tool within the haptic volume and provide haptic feedback to constrain movement of the cutting tool outside of the haptic volume.

2. The system of claim 1 wherein the tapered section of the haptic volume is a conical section.

3. The system of claim 2 wherein a half vertex angle of the conical section ranges from about 10° to about 30°.

4. The system of claim 2 wherein a vertex angle of the conical section ranges from about 12° to about 23°.

5. The system of claim 2 wherein a vertex angle of the conical section ranges from about 15° to about 20°.

6. The system of claim 2 wherein a half vertex angle of the conical section ranges from about 16° to about 19°.

7. The system of claim 1 wherein the tapered section of the haptic volume is a parabolic section.

8. The system of claim 7 wherein a radius r(h) of an outer surface of the parabolic section is defined by Equation 1:

$$r(h) \leq R - \sqrt{R^2 - h^2} \text{ when } h \text{ is } < R \qquad (1)$$

wherein R is the radius of the intended indentation and h is a distance between an outer surface of the bone and r on the outer surface of the parabolic section.

9. The system of claim 1 wherein the haptic volume generated by the controller further includes a straight-line section disposed between the tapered section and the bone.

10. The system of claim 9 wherein the straight-line section has a length less than or equal to about 6 mm.

11. The system of claim 9 wherein the straight-line section has a length ranging from about 2 to about 4 mm.

12. The system of claim 1 wherein the haptic volume further includes a straight line section between the tapered section and the bone.

13. A haptic robotic surgical system for total hip arthroplasty (THA) surgeries, the system comprising:
a cutting tool including a central axis aligned with a bottom center of the cutting tool; and
a controller programmed to:
compare an intended indentation in the acetabulum and a position of the cutting tool when initially placed on the acetabulum, the central axis of the cutting tool being offset from a central axis of the intended indentation;
generate a haptic volume through the acetabulum based at least in part on the comparison of the intended indentation in the acetabulum and the position of the cutting tool when initially placed on the acetabulum, the haptic volume including a tapered section that narrows as the haptic volume extends inward through the acetabulum and a straight line section disposed between the tapered section and the acetabulum; and
generate control signals that will allow movement of the cutting tool within the haptic volume and provide haptic feedback to constrain movement of the cutting tool to within the haptic volume.

14. The system of claim 13 wherein the controller is further programmed to stop rotation of the cutting tool when the cutting tool is moved outside of the haptic volume.

15. The system of claim 14 wherein the haptic volume comprises a conical section having a vertex and a straight line path extending towards the acetabulum from the vertex.

16. The system of claim 14 wherein the haptic volume comprises a parabolic section having a vertex and a straight line path extending towards the acetabulum from the vertex.

17. The system of claim 16 wherein a radius r(h) of an outer surface of the parabolic section is defined by Equation 1:

$$r(h) \leq R - \sqrt{R^2 - h^2} \text{ when } h \text{ is } < R \qquad (1)$$

wherein R is the radius of the intended indentation and h is a distance between an outer surface of the acetabulum and r on a surface of the parabolic section.

* * * * *